US 6,610,032 B1

(12) United States Patent
Prody

(10) Patent No.: US 6,610,032 B1
(45) Date of Patent: Aug. 26, 2003

(54) SURGICAL DRAINAGE DEVICE

(75) Inventor: MaryAnn Robinson Prody, Boca Raton, FL (US)

(73) Assignee: Dale Medical, Inc., Plainville, MA (US)

( * ) Notice: Subject to any disclaimer, the term of this patent is extended or adjusted under 35 U.S.C. 154(b) by 152 days.

(21) Appl. No.: 09/643,104

(22) Filed: Aug. 21, 2000

Related U.S. Application Data

(60) Provisional application No. 60/150,090, filed on Aug. 20, 1999.

(51) Int. Cl.[7] .................................................. A61M 5/32
(52) U.S. Cl. ....................................... 604/179; 604/345
(58) Field of Search .............................. 604/179, 327, 604/345; 224/148.1, 148.2, 148.4, 148.5, 148.6, 148.7, 269, 663, 682

(56) References Cited

U.S. PATENT DOCUMENTS

| | | | | |
|---|---|---|---|---|
| 4,122,851 A | * | 10/1978 | Grossner ..................... | 128/295 |
| 4,139,130 A | | 2/1979 | Glusker et al. ............ | 224/5 W |
| 4,435,171 A | | 3/1984 | Goldberg et al. ............ | 604/49 |
| 4,511,358 A | | 4/1985 | Johnson, Jr. et al. ....... | 604/327 |
| D282,694 S | | 2/1986 | Gault ......................... | D2/381 |
| 4,582,508 A | | 4/1986 | Pavelka ...................... | 604/179 |
| 4,606,736 A | | 8/1986 | Van de Weghe ............ | 604/322 |
| 4,665,566 A | | 5/1987 | Garrow ......................... | 2/171 |
| D290,306 S | | 6/1987 | Pickens ....................... | D2/630 |
| 4,738,661 A | | 4/1988 | Marut ........................ | 604/179 |
| 4,799,923 A | | 1/1989 | Campbell ................... | 604/179 |
| 4,819,846 A | | 4/1989 | Hannemann ................ | 224/240 |
| 4,917,280 A | | 4/1990 | Schneider ................... | 224/223 |
| 4,957,231 A | * | 9/1990 | Kalisher ..................... | 224/151 |
| 5,016,291 A | | 5/1991 | Capper ........................... | 2/312 |
| 5,048,512 A | | 9/1991 | Turner et al. ............... | 128/876 |
| 5,053,027 A | | 10/1991 | Manfredi .................... | 604/327 |
| 5,087,251 A | | 2/1992 | Heyman et al. ............ | 604/327 |
| 5,234,420 A | | 8/1993 | Horton et al. ............... | 604/345 |
| 5,244,464 A | | 9/1993 | Madden et al. ............. | 604/179 |
| 5,263,941 A | | 11/1993 | Cockrill ....................... | 604/179 |
| 5,271,745 A | | 12/1993 | Fentress et al. ............. | 604/179 |

(List continued on next page.)

FOREIGN PATENT DOCUMENTS

| | | | | |
|---|---|---|---|---|
| WO | WO 94/12231 | 6/1994 | .......... | A61M/16/00 |

OTHER PUBLICATIONS

Baxter Healthcare Corporation Instruction Sheet, Jackson–Pratt® "Closed Wound Suction Drainage Systems" Copyright 1991 (2 pages).

*Primary Examiner*—Weilun Lo
*Assistant Examiner*—Michael Bogart

(57) ABSTRACT

A belt extends about the waist of a patient and is secured at a selected tightness thereon, the securing device being adjustable as to tightness. An outside surface of the belt provides plural spaced apart elongate fasteners aligned with a longitudinal axis of the belt, each of the fasteners comprising a first surface attachment element integral with the outside surface of the belt, and a second surface attachment element permanently fastened at one end of the first surface attachment element and extending longitudinally in removable, mutually engaged contact with the first surface attachment element. A fluid storing bulb has an inlet nipple adapted for receiving a fluid conduit for conducting a bodily fluid into the bulb, and has an outlet nipple adapted for expulsing the fluid collected. A stopper, temporarily seals the outlet nipple when it is not in use. An attachment band provides a loop adapted for receiving one of the second surface attachment elements for engaging the fluid storing bulb with the belt within reach of a person wearing the belt. A fluid conduit engages the inlet nipple of the fluid storing bulb at one end, and at the other end, the source of the bodily fluid.

14 Claims, 2 Drawing Sheets

U.S. PATENT DOCUMENTS

| | | | |
|---|---|---|---|
| D345,052 S | 3/1994 | Stokke et al. | D3/228 |
| 5,320,097 A | 6/1994 | Clemens et al. | 128/207.17 |
| 5,403,285 A | 4/1995 | Roberts | 604/179 |
| 5,425,719 A | 6/1995 | Lessing, Jr. | 604/179 |
| 5,468,229 A | 11/1995 | Chandler | 604/179 |
| 5,496,282 A | 3/1996 | Militzer et al. | 604/179 |
| 5,515,866 A | 5/1996 | Somers | 128/845 |
| 5,643,233 A * | 7/1997 | Turner | 604/332 |
| 5,643,236 A | 7/1997 | Hadley | 604/353 |
| 5,669,884 A | 9/1997 | Bennes et al. | 604/179 |
| 5,672,159 A | 9/1997 | Warrick | 604/179 |
| 5,683,022 A * | 11/1997 | Evans | 224/583 |
| 5,688,248 A | 11/1997 | Lessing, Jr. | 604/179 |
| 5,716,344 A | 2/1998 | Kiel | 604/174 |
| 5,728,070 A | 3/1998 | Walker et al. | 604/179 |
| D395,151 S | 6/1998 | Maddox | D2/614 |
| 5,776,105 A | 7/1998 | Corn | 604/174 |
| 5,853,396 A | 12/1998 | Bennes et al. | 604/179 |
| 5,897,519 A | 4/1999 | Shesol et al. | 602/79 |
| 5,941,856 A | 8/1999 | Kovacs et al. | 604/179 |
| 5,961,501 A | 10/1999 | Cassidy et al. | 604/327 |
| 5,980,498 A | 11/1999 | Brown et al. | 604/327 |
| 5,980,499 A | 11/1999 | Ekey | 604/345 |
| 6,045,542 A | 4/2000 | Cawood | 604/327 |
| 6,126,639 A | 10/2000 | Sutherland et al. | 604/179 |
| 6,129,709 A | 10/2000 | Millen | 604/179 |
| D433,227 S | 11/2000 | Evans | D3/218 |
| 6,152,915 A | 11/2000 | Watson et al. | 604/540 |
| 6,168,578 B1 | 1/2001 | Diamond | 604/29 |
| 6,270,485 B1 * | 8/2001 | Ekey | 604/345 |
| 6,279,804 B1 * | 8/2001 | Gregg | 224/675 |

* cited by examiner

SURGICAL DRAINAGE DEVICE

The present application claims the filing date of a previously filed provisional patent application having Ser. No. 60/150,090 and an assigned filing date of Aug. 20, 1999 and which contains subject matter substantially the same as that described and claimed in the present application.

BACKGROUND OF THE INVENTION

1. Field of the Invention

This invention relates generally to surgical drainage devices and more particularly to an apparatus for draining a surgical wound whereby one or more drainage reservoirs is easily and securely fastened to a belt within sight and reach of the patient.

2. Description of Related Art

The following art defines the present state of this field:

Pickens, U.S. D290,306 describes a combined belt and tennis ball holder.

Campbell, U.S. Pat. No. 4,799,923 describes a medical tube securing device, for securing tubes such as gastrostomy tubes which project from a person's body, and comprises an openable pouch having a hole in the back portion thereof. A tube is pulled through the hole in the pouch, the pouch is secured to the body of the user, and the pouch is closed, thereby enclosing therewithin the free portion of the tube. In this manner, the portion of the tube projecting from the user's body is neither susceptible to being pulled by the user's hands, nor likely to be engaged by objects around the user; hence, the incidence of accidental, premature removal of the tube is greatly reduced. In an alternate embodiment, fasteners are also provided to reduce the possibility of the tube sliding into the user's body.

Hannemann, U.S. Pat. No. 4,819,846 describes an article of sportsman's equipment for use by sportsmen engaged in endurance oriented activities such as marathons, etc., in which a plurality, generally from four to eight pouches for nutrients, are provided on a belt. The belt and pouches are made of flexible sheet material having a weight of not more than 7.5 ounces/sq.yd. and preferably from about 1.75 to about 6.0 ounces/sq.yd.

Madden et al., U.S. Pat. No. 5,244,464 describes a band for securing and aligning medical tubing relative a portion of a human body including primary and secondary straps constructed of Velcro™. The primary strap includes a male Velcro™ portion fastened to the foam substrate of the Velcro™ so that the primary strap can be adjustably fastened to itself about a portion of a human body. The secondary strap includes one or more male Velcro™ portions attached to the foam substrate of the Velcro™. The secondary strap attaches at its ends anywhere along the primary strap, trapping the medical tubing between its ends and the primary strap to secure the medical tubing in place.

Fentress et al., U.S. Pat. No. 5,271,745 describes medical tubing retaining device and method to use the same. More particularly, it relates to a one-piece flexible band containing members to form a sling. The sling is of sufficient length to retain coiled medical tubing when affixed to the band. This device is used to retain tubing from indwelling devices such as catheters.

Roberts, U.S. Pat. No. 5,403,285 describes an apparatus for holding a catheter of a type having a flexible tube which can have one end thereof which extends into a large vein near a heart. The tube has a closure cap on the other end thereof for allowing the introduction of medications or fluids into the blood in the tube so that they can be quickly mixed with blood and thereby transported to other parts of the body for permitting blood to be quickly withdrawn therefrom. An elongated, flexible, elastic member is adapted to extend completely around the chest of a person and over the flexible tube at the location where the tube exits the body. Hook and loop closure members are provided on the flexible members for holding the tube in a coiled position adjacent the flexible member. The flap is provided with hook and loop fasteners for selectively covering up the coiled tube when not in use, but allowing easy access to the tube for adding medications, drawing blood, or to change the entire securing apparatus from time to time so that it can be washed, cleaned and re-used. Also, elastic and has hook and loop fasteners on the ends thereof so that it can be easily stretched and fastened around the chest.

Militzer et al., U.S. Pat. No. 5,496,282 describes a belt for stabilizing an implanted peritoneal dialysis catheter exiting from the abdomen of a user and having a valve at one end. The belt includes a body of elasticized fabric designed to encircle the patient, two fasteners with hook and pile features, and a receptacle. In addition, a relatively small adhesive-backed member, having adhesive on its inner surface and having a pile member on its outer surface, surrounds a portion of the catheter tubing at a point near where the tubing exits the user. One of the two fasteners secures and stabilizes the tubing to the belt body by pressing against the pile outer surface of the adhesive-backed member and subsequently is secured to itself. The second fastener is used to further secure the tubing against the belt body at a distance from the one fastener. The receptacle, or envelope, integral to the belt body, is used to securely hold the valve end of the catheter against the belt body. The method of using the present invention is also described.

Clemens, W094/12231 describes an endotracheal tube holding and securing device, adjustable using a strap including mating hook and loop type fastener pads, which is used to hold an endotracheal tube in place after intubation has been performed. The endotracheal tube holder includes two identical hook-shaped members each having a hook portion. One hook-shaped member is inverted, superimposed and slidably connected to the second hook-shaped member. In this orientation, the curved faces of the hook-shaped members form a "C" shaped gripper used for holding the endotracheal tube. The strap is used to both secure the endotracheal tube holder to the patient's face and to apply a force at the end of each hook-shaped member to cause each member to slide in the direction of the applied force, causing the tube to be firmly gripped between the two curved faces of the holder.

The prior art teaches the use of belts for supporting tubing and holding medical devices. However, the prior art does not teach a belt having elongate surface fasteners positioned at the front of the belt and adapted for securing loops of drainage bulbs that are transparent for visual recognition of fill levels. The present invention fulfills these needs and provides further related advantages as described in the following summary.

SUMMARY OF THE INVENTION

The present invention teaches certain benefits in construction and use which give rise to the objectives described below.

A belt extends about the waist of a patient and is secured at a selected tightness thereon, the securing means being adjustable as to said tightness. An outside surface of the belt provides plural spaced apart elongate fasteners aligned with a longitudinal axis of the belt, each of the fasteners comprising a first surface attachment element integral with the outside surface of the belt, and a second surface attachment element permanently fastened at one end of the first surface attachment element and extending longitudinally in removable, mutually engaged contact with the first surface attachment element. A fluid storing bulb has an inlet nipple adapted for receiving a fluid conduit for conducting a bodily fluid into the bulb, and has an outlet nipple adapted for expulsing the fluid collected. A stopper, temporarily seals the outlet nipple when it is not in use. An attachment band provides a loop adapted for receiving one of the second surface attachment elements for engaging the fluid storing bulb with the belt within reach of a person wearing the belt. A fluid conduit engages the inlet nipple of the fluid storing bulb at one end, and at the other end, the source of the bodily fluid.

A primary objective of the present invention is to provide a drainage belt having advantages not taught by the prior art.

Another objective is to provide such a belt capable of holding plural drainage devices within view of the wearer.

A further objective is to provide such a belt capable, of quick and easy replacement of the drainage devices.

A still further objective is to provide such a belt capable of supporting drainage devices at waist level.

A final objective is to provide such a belt whereby the status of fill of the drainage device is visible.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the present invention. In such drawings.

DETAILED DESCRIPTION OF THE INVENTION

Figure 1:
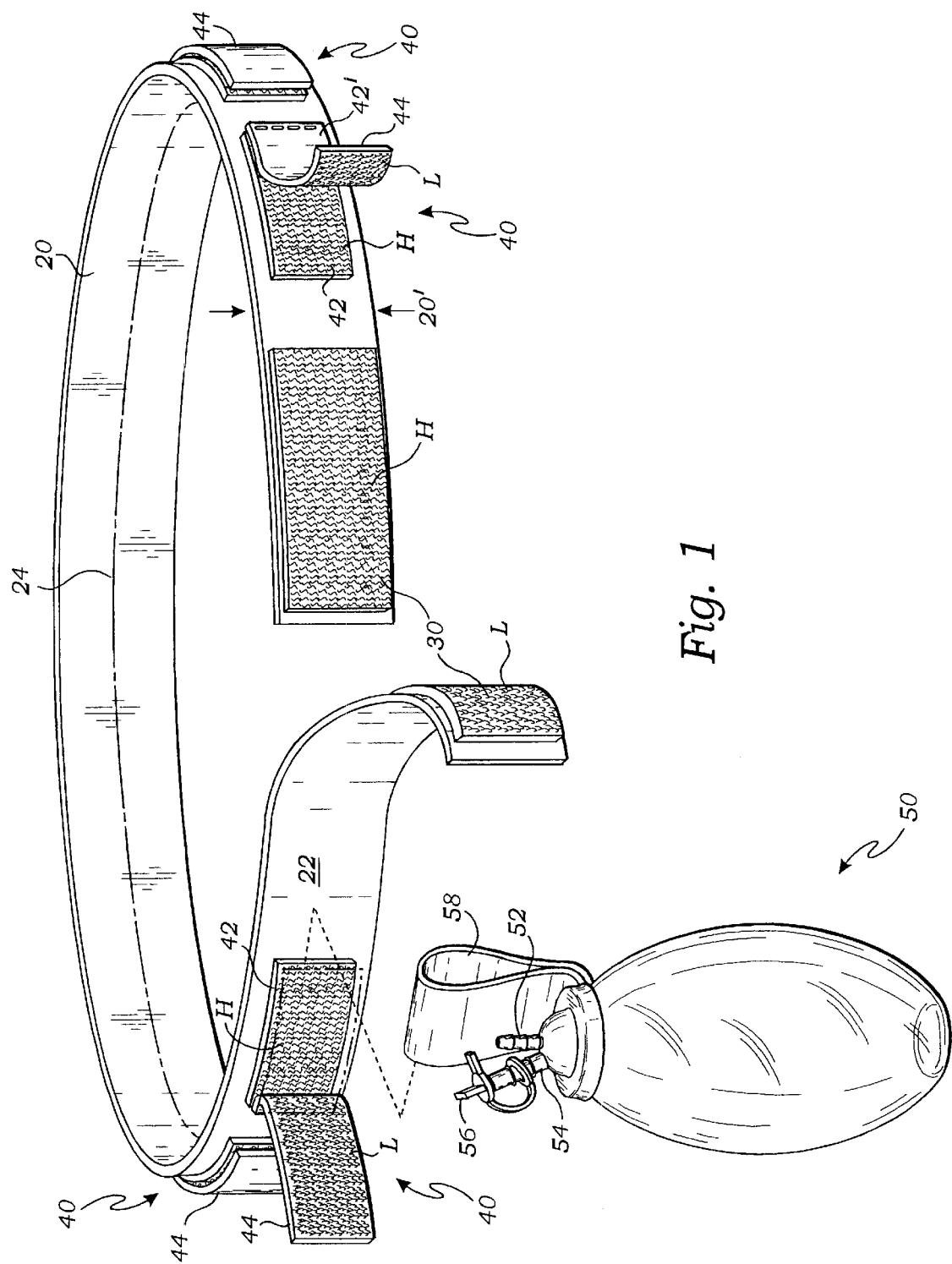
FIG. 1 is a perspective view of the preferred embodiment of the invention.

The invention, as shown in the figures is an apparatus for collecting a bodily fluid 10 in a medical draining procedure, the apparatus comprising a belt 20 adapted by its size for extending about the waist of a patient and including a belt fastening means 30, such as any common belt fastener, for securing the belt 20 at a selected tightness thereon, the belt fastening means 30 being adjustable as to said tightness. An outside surface 22 of the belt 20, i.e., the surface of the belt that faces outwardly when the belt is in place, as worn, provides plural spaced apart elongate fasteners 40 (fasteners) aligned with the longitudinal axis 24 of the belt 20. Each of these fasteners 40 comprise a first surface attachment element 42 integral with the outside surface 22 of the belt 20, and a second surface attachment element 44 permanently fastened, as by sewing, at one end 42' of the first surface attachment element 42 and extending along the longitudinal axis 24 in separable but normally mutually engaged contact with the first surface attachment element 42. This positioning of the fasteners 40 is critical to the successful operation of the invention in that the fastener 40 may be made as long as necessary for the successful attachment of a loop of a selected width as described below.

If the fastener 40 is positioned and closed in a direction counter to the longitudinal axis of the belt 20, that is crosswise to the direction of the belt 20, such as is taught in Hannemann U.S. Pat. No. 4,819,846, Fentress et al U.S. Pat. No. 5,271,745, Roberts U.S. Pat. No. 5,403,285, Militzer et al U.S. Pat. No. 5,496,282, an artificial limitation is imposed by virtue of the practical width that the belt 20 can have. A belt 20 that is too wide tends to wrinkle and roll-over onto itself due to the flexure of the human body. This, then, creates a problem in unrolling the belt in order to gain access to the fastener to open it for attachment and detachment of items supported by the fastener 40. That is, the width 20' of the belt 20 then becomes the limiting factor as to how long the fastener 40 can be. The length of the fastener 40, in turn, determines how much fastener material can be used for sealing the fastener. Clearly, the longer the fastener the more holding power it can have for a given pounds per square inch of closure strength. The belt fastening closure 30 is oriented in the longitudinal direction of belt 20 primarily for adjustability of the belt 20 about a given size waist. However, longitudinally oriented closures of the type described here are not found in the prior art, and this aspect is considered novel and of improved benefit to the user.

A fluid storing means 50 provides an inlet nipple 52 adapted for receiving a fluid conduit 60 for conducting the bodily fluid 10 to the fluid storing means 50. The fluid storing means further provides an outlet nipple 54 adapted for expulsing the bodily fluid 10 collected within the fluid storing means 50. The outlet nipple 54 provides a stopper 56 for temporarily sealing the outlet nipple 54 when the outlet nipple is not in use. The fluid storing means 50 further provides an attachment band 58 comprising a loop adapted by it attitude or position relative to the center of mass of the storing means 50, and width, for receiving one of said second surface attachment elements 44 for engaging the fluid storing means 50 with the belt 20 for disposing the fluid storing means 50 within visual sight and physical reach of the patient wearing the belt 20.

The fluid conduit 60 is engaged at one terminal end thereof 62 with the inlet nipple 52 of the fluid storing means 50 and is engaged at the other terminal end thereof 64 with a source of the bodily fluid.

Preferably, the belt 20 is of an elastic material for stretch adjustment to fit a range of waist sizes. Preferably, the fluid storing means 50 is a flexible bulb enabled by its flexibility for expulsion of the fluid 10 stored therein by manually compressing the bulb. It is highly desirable that the fluid storing means 50 is of a transparent material, such as a clear plastic or rubber, so as to enable the patient to see when the bulb is filled so a to know that it must be emptied. In the preferred embodiment, the plural spaced apart elongate fasteners 40 comprise two such fasteners on each side of the belt fastening means 30, the elongate fasteners 40 being placed frontally within the normal sight range of the patient. Preferably, the attachment elements of both the belt 20 and the elongate fasteners 40 comprise a surface of outwardly directed hooking structures "H" and the second surface attachment element comprises a surface of outwardly directed looping structures "L", wherein the hooking structures H and the looping structures L are adapted for mutual engagement through contact. This type of fastener is well known by the trademark Velcro™ but may be any such similar surface contact fastening material as is known and available in the commercial marketplace.

Figure 2:
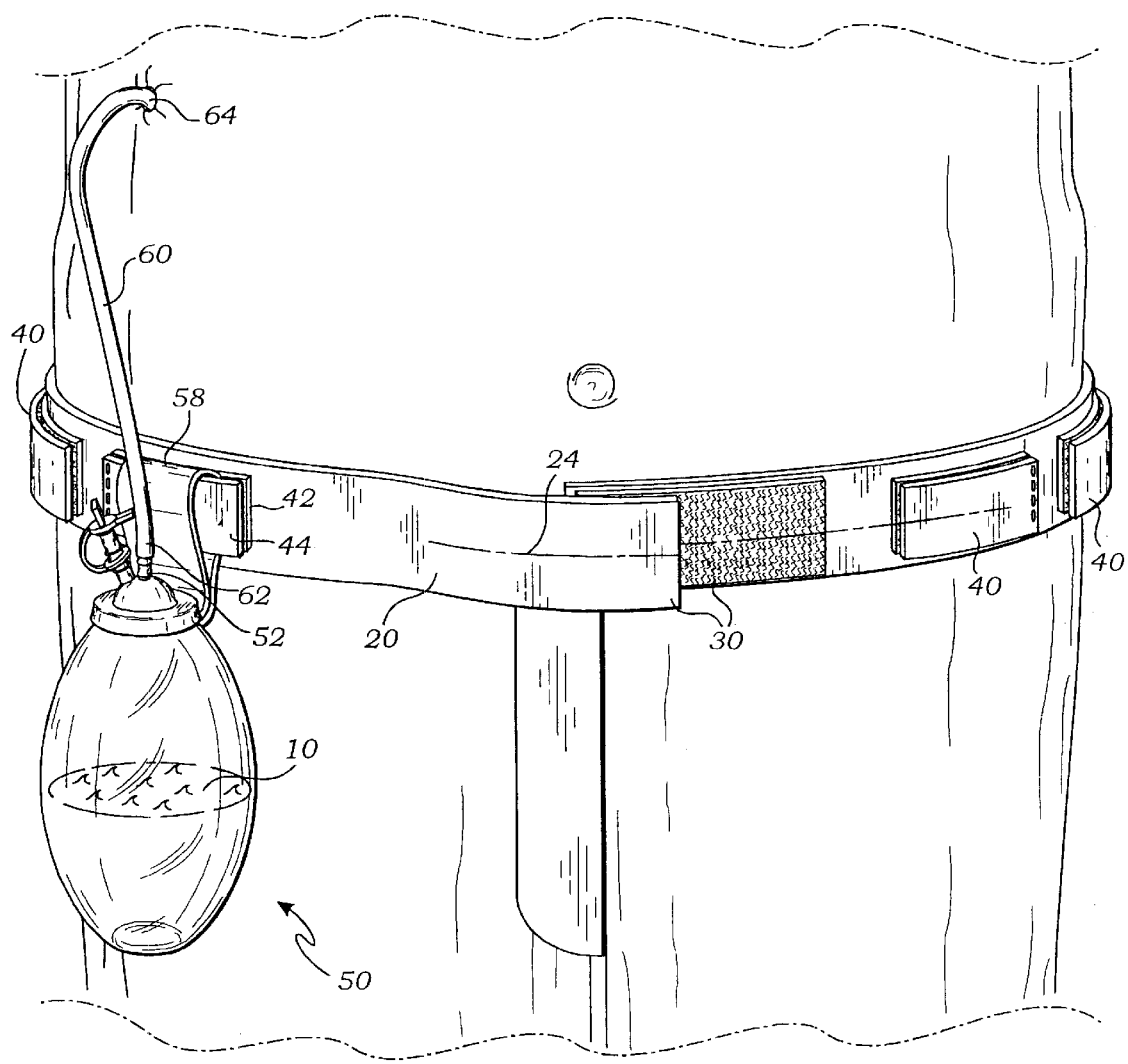
FIG. 2 is a perspective view of the invention in use.

In operation, the belt 20 is placed about the waist of the patient and fastened at the front using fastener 30. One of the second surface attachment elements 44 of one of the elongate fasteners 40 is manually pulled away from its companion first attachment element 42 so that it is free although the two elements are permanently joined at one common end 42'. The second attachment element 44 is hinged outwardly, as shown at the left of FIG. 1, and threaded through the loop of the attachment band 58 of the fluid storing means 50. This procedure may be followed for attaching additional fluid storing means 50 to the others of the elongate fasteners 40 so as to mount these storage devices within visual range of the patient. The fluid conduits 60 are then engaged with the fluid storage means 50, as shown in FIG. 2, so as to enable drainage from the patient. When the fluid storing means 50 are filled they may be removed from the belt 20, in the reverse manner as described for attachment thereof, and drained by removing the stopper 56 from the outlet nipple 54 and compressing the bulb thereby driving the fluid out of the bulb. The Fluid storing means 50 need not be disconnected from the fluid conduit 60 when being emptied.

While the invention has been described with reference to at least one preferred embodiment, it is to be clearly understood by those skilled in the art that the invention is not limited thereto. Rather, the scope of the invention is to be interpreted only in conjunction with the appended claims.

What is claimed is:

1. An apparatus for collecting a bodily fluid in a medical draining procedure, the apparatus comprising:
   a belt adapted for extending about the waist of a patient including a belt fastening means for securing the belt at a selected tightness thereon, the securing means being adjustable as to said tightness;
   an outside surface of the belt providing plural spaced apart elongate fasteners aligned with a longitudinal axis of the belt, each of the fasteners comprising a first surface attachment element integral with the outside surface of the belt, and a second surface attachment element permanently fastened at one end of the first surface attachment element and extending longitudinally in removable, mutually engaged contact with the first surface attachment element;
   a fluid storing means providing an inlet nipple receiving a fluid conduit for conducting a bodily fluid to the fluid storing means, the fluid storing means further providing an outlet nipple adapted for expulsing the bodily fluid collected within the fluid storing means, the outlet nipple providing a stopper for temporarily sealing the outlet nipple when the outlet nipple is not in use, the fluid storing means further providing an attachment band comprising a loop adapted for receiving one of said second surface attachment element for engaging the fluid storing means with the belt for disposing the fluid storing means within reach of a person wearing the belt;
   the fluid conduit engaged at one terminal end thereof with the inlet nipple of the fluid storing means and engaged at the other terminal end thereof with a source of the bodily fluid.

2. The apparatus of claim 1 wherein the belt is of an elastic material for stretch adjustment to fit a range of waist sizes.

3. The apparatus of claim 1 wherein the fluid storing means is a flexible bulb enabled for expulsion of the fluid stored therein by compressing the bulb.

4. The apparatus of claim 1 wherein the fluid storing means is of a transparent material so as to enable the individual to see when the bulb is filled.

5. The apparatus of claim 4 wherein the plural spaced apart elongate fasteners comprise at least one such fasteners on each side of the belt fastening means, the elongate fasteners placed frontally so as to be within normal visual access of the individual.

6. The apparatus of claim 1 wherein the first surface attachment element comprises a surface of outwardly directed hooking structures and the second surface attachment element comprises a surface of outwardly directed looping structures, wherein the hooking structures and the looping structures are adapted for mutual engagement through contact.

7. A device for supporting one or more fluid reservoirs attached to a patient, each fluid reservoir having an aperture associated therewith for supporting the fluid reservoir, the device comprising:
   a belt to be attached about the torso of the patient; and
   a plurality of fasteners attached to the belt, wherein each fastener is for removably attaching one of said fluid reservoirs to the belt and includes a first end permanently attached to the belt and a second end adapted to releasably engage the belt, each fastener adapted to removably attach a fluid reservoir to the belt by threading said second end through said aperture and engaging said second end to the belt.

8. The device of claim 7, wherein each fastener is substantially aligned with a longitudinal axis of the belt.

9. The device of claim 7, wherein the second end of each fastener includes one of a hook and loop fastener to releasably engage the belt.

10. The device of claim 7, wherein the aperture is a loop attached to the fluid reservoir.

11. The device of claim 9, wherein the belt includes a plurality of attachment elements respectively associated with each fastener, each attachment element being integral with the belt to releasably engage the second end of the fastener associated therewith.

12. The device of claim 11, wherein each attachment element is a loop surface sewn to the belt.

13. The device of claim 9, wherein the second end of each fastener includes a hook surface for engaging a loop surface on the belt.

14. The device of claim 7, wherein the first end is sewn to the belt.

* * * * *